(12) United States Patent
Wu et al.

(10) Patent No.: US 8,686,187 B2
(45) Date of Patent: Apr. 1, 2014

(54) ETHOXY DIPHENYL ETHANE DERIVATIVES, PREPARATION PROCESSES AND USES THEREOF

(75) Inventors: Fanhong Wu, Shanghai (CN); Fanhua Xiao, Shanghai (CN); Weiguo Zhou, Dongyang (CN); Fangming Xu, Dongyang (CN)

(73) Assignees: Shanghai Ecust Biomedicine Co., Ltd., Xuhui, Shanghai (CN); Zhejiang Wild Wind Pharmaceutical Co. Ltd., Beijiang Industrial Zone Dongyang, Zhejiang (CN)

( * ) Notice: Subject to any disclaimer, the term of this patent is extended or adjusted under 35 U.S.C. 154(b) by 224 days.

(21) Appl. No.: 13/124,504

(22) PCT Filed: Oct. 15, 2009

(86) PCT No.: PCT/CN2009/074474
§ 371 (c)(1),
(2), (4) Date: Oct. 19, 2011

(87) PCT Pub. No.: WO2010/043180
PCT Pub. Date: Apr. 22, 2010

(65) Prior Publication Data
US 2012/0046492 A1    Feb. 23, 2012

(30) Foreign Application Priority Data
Oct. 15, 2008 (CN) .......................... 2008 1 0201182

(51) Int. Cl.
C07C 233/05 (2006.01)
C07C 217/84 (2006.01)
C07C 237/20 (2006.01)
C07C 231/08 (2006.01)
C07C 213/02 (2006.01)

(52) U.S. Cl.
USPC .............. 564/196; 564/443; 562/23; 568/644

(58) Field of Classification Search
USPC ................ 564/196, 443; 562/23; 568/644
See application file for complete search history.

(56) References Cited

U.S. PATENT DOCUMENTS

| | | | |
|---|---|---|---|
| 5,430,062 A * | 7/1995 | Cushman et al. | ............. 514/646 |
| 6,054,598 A | 4/2000 | Sachdeva et al. | |
| 2003/0220404 A1 * | 11/2003 | Mutti et al. | ................... 514/646 |
| 2009/0170956 A1 | 7/2009 | Shen | |

FOREIGN PATENT DOCUMENTS

CN    101139358 A    3/2008

OTHER PUBLICATIONS

Cushman et al, J. of Medicinal Chemistry, 1992, 35(12), 2293-306.*
International Search Report for International Application No. PCT/CN2009/074474, The State Intellectual Property Office, the P.R. China, mailed Jan. 21, 2010.

* cited by examiner

*Primary Examiner* — Shailendra Kumar
(74) *Attorney, Agent, or Firm* — Daniel J. Nevrivy; Keisha Hylton-Rodic; Nevrivy Patent Law Group P.L.L.C.

(57) ABSTRACT

The invention discloses an ethoxydiphenylethane derivative and a synthetic method and uses thereof 4' position of phenylethane B aromatic ring is chemically modified by ethoxy and hydroxy at position 3' thereof is simultaneously modified to water soluble prodrug such as phosphate, and similarly, amino acid side chain is introduced to amino at position 3' to form amino acid amide water soluble prodrug having the structure shown as formula (I)

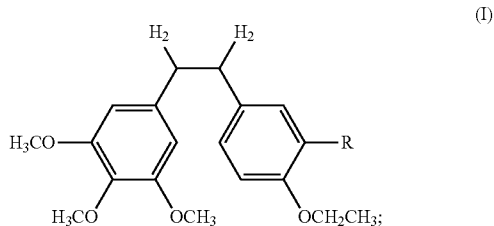

the ethoxydiphenylethane derivative and the prodrug thereof include strong tubulin aggregation inhibiting ability and obvious target damage effect for tumor vessels, selectively cause dysfunction and structural damage of tumor vessels and induce apoptosis of vascular endothelial cells in order to play the role of killing tumor cells or inhibiting tumor metastasis in case that the tumor cells are free from the support of nutrition and oxygen.

18 Claims, 2 Drawing Sheets

ETHOXY DIPHENYL ETHANE DERIVATIVES, PREPARATION PROCESSES AND USES THEREOF

This application is a 371 of PCT/CN09/74474, filed Oct. 15, 2009.

TECHNICAL FIELDS

The invention relates to the field of drug synthesis, especially to the synthesis of diphenylethane derivative anticancer drug.

BACKGROUND ARTS

A novel tubulin depolymerizing factor found recently can cause vascular occlusion at the dose lower than MTD (Expert Opin lnvestig Drugs.2004 September; 13(9) 1171-82). In 2005, Loin Vincent et al. came up with a novel tubulin depolymerizing factor with similar attributes that can, as vascular target agents (VTAs), damage tubulin skeleton, and documental data shows that the vascular target agents can selectively induce deterioration of tumor vessels, partially through VE-cadherin signal paths. Such a tubulin depolymerizing factor causes selective damage to tumor vessels and prevents angiogenesis of tumor without having an influence on normal vascular system. Meanwhile, it can inhibit aggregation of tubulin, selectively cause dysfunction and structural damage of tumor vessels and induce apoptosis of vascular endothelial cells in order to play the role of killing tumor cells or inhibiting tumor metastasis in case that the tumor cells are free from the support of nutrition and oxygen.

In 2005, GillianM.Tozer et al. reported in the influential magazine *Nature Rev Cancer* that: such compounds have an influence not only on the proliferation of vascular endothelial cells, but also on the migration of endothelial cells to further rapidly change the morphology of vascular endothelial cells, lead to the apoptosis of endothelial cells and break off the connection of vascular endothelial cells, thereby rapidly causing dysfunction and structural damage of tumor vessels. Since normal vessels are all supported by smooth muscle cells generally, such compounds that only act on the vessels without the support of smooth muscle cells have no influence on smooth muscle-supported vessels, in order to rapidly and selectively cause dysfunction and structural damage of tumor vessels to further selectively act on tumor cells and greatly reduce toxicity to normal cells (Nat rve Canaer.2005 June; 5 (6) 423-35, *J. Clin. Invest.*, Novenber 1, 2005; 115(11), 2992-3006). Such drugs are considered to be one of the most promising antitumor drugs at present.

Currently, among all the domestic and overseas researches on such drugs, only CombretastatinA-4 diphenylethylene compounds are put into clinical research, the patent of invention entitled 'ethoxycombretastatin and preparation and uses of prodrug thereof' (International Publication Number WO2008/031333A1) discloses that diphenylethylene B aromatic ring position 4' alkoxy of CombretastatinA-4 is an active action site, original methyl at diphenylethylene B aromatic ring position 4' is modified to ethyl that can form an active target with hydroxy, amino and other groups at position 3', thus the target activity thereof for tumor vessels can be enhanced. However, owing to double-bond connection, family units in cis-configuration in Combretastatin causes the most effective damage to tumor vessels while family compounds in trans-configuration have no inhibiting effect on tumors. Cis-trans isomerization reaction exists and trans-configuration brings no drug effect but certain toxic and side effects, so the requirements of separation and purification technologies are high, the column chromatography is required, the consumption of now materials is large, the technological cost is high, the yield is low, and simultaneously, diphenylethylene compounds are transformed to trans-configuration through ultraviolet illumination and are required to be stored away from sunlight at low temperature, hence, the storage and actual application of the diphenylethylene compounds are extremely difficult.

The patent (Cushman,Mark et al. Synthesis and evaluation of analogs of (Z)-1-(4-methoxyphenyl)-2-(3,4,5-trimethoxyphenyl)ethane as potential cytotoxic andantimitotic agents, Journal of Medicinal Chemistry, 1992, Vol. 35, No. 12, 2293-306) discloses a compound, i.e. (Z)-1-(3,4,5-trimethoxy)phenyl-2-(4'-ethoxy)phenylethylene, however, synergistic active target cannot be formed as substituted groups such as —OH, —NH2 are not present at position 3', and the anticancer drug effect gradually decreases from 4'-methoxy, ethoxy, propoxy at position 4'; and U.S. Pat. No. 6,054,598 discloses a synthetic method for modifying 2-methoxyestradiol to 2-ethoxyestradiol, 2-ethoxyestradiol includes the in vitro anticancer activity 1000 times as much as 2-methoxyestradiol; and researches have found that: ethoxydiphenylethane derivatives, 4'-ethoxy and 3'-hydroxy, amino have the same synergistic effect and can obviously enhance anticancer effect, but the anticancer effect thereof is remarkably lowered subsequent to the modification at position 4' by propoxy.

Invention Contents:

1. The invention provides an ethoxydiphenylethane derivative, having the structure shown as the formula (I):

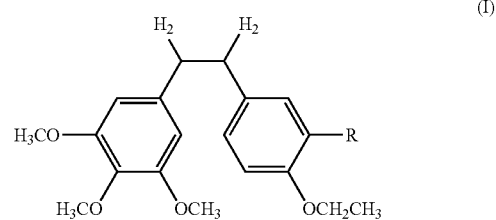

(I)

Wherein, the R is hydroxy, amino, phosphate, sulfate, choline phosphate, or amino acid side chain and water soluble ammonium salt thereof.

The R preferably is hydroxy, amino, disodium phosphate salt, ammonium phosphate salt, sulfate salt, choline phosphate inner salt, natural amino acid side chain and water soluble ammonium salt thereof, or —NH(COCHR'NH)m-H (wherein R' is hydrogen, phenyl, and m represents an integer from 1 to 3) and water soluble ammonium salt thereof.

In preferred embodiments, the R is —OH, —NH$_2$, —OPO$_2$Na$_2$, —NHCOCH$_2$NH$_2$ or —NHCOCHNH$_2$CH$_2$OH.

2. The invention discloses a preparation method of hydroxyethoxydiphenylethane derivative in the compound of the formula (I), which comprises the steps that:

(1) Under phase transfer catalysis, 4-hydroxy-3-methoxybenzaidehyde is subjected to ethoxylation by bromethyl to form 4-ethoxy-3-methoxybenzaldehyde III;

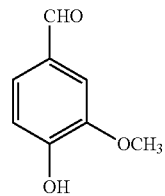

II

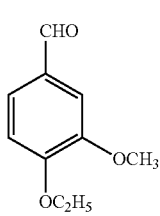

(2) meta-methyl is selectively removed by lithium diphenylphosphide and converted to hydroxy in order to obtain 4-ethoxy-3-hydroxybenzaldehyde IV;

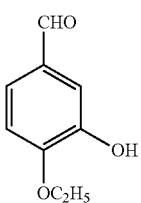

(3) The 4-ethoxy-3-hydroxybenzaldehyde IV is prepared to 4-ethoxy-3-benzyloxybenzaldehyde V by benzyl chloride;

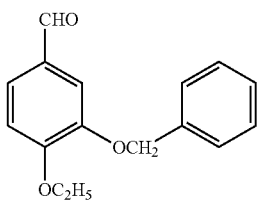

(4) 3,4,5-trimethoxy triphenyl benzylidene bromide phosphonium bromide tetrahydrofuran solution and 4-ethoxy-3-benzyloxybenzaldehyde are subjected to vinylation addition under the addition of potassium tert-butoxide in order to synthesize 3,4,5-trimethoxy-3'-benzyloxy-4'-ethoxydiphenylethylene VI;

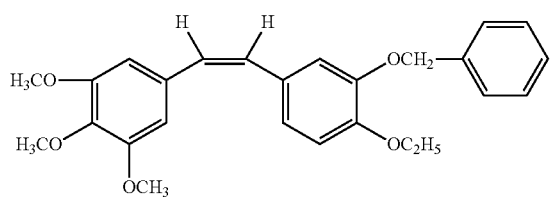

(5) the 3,4,5-trimethoxy-3'-benzyloxy-4'-ethoxydiphenyl-ethylene (VI) is hydrogenated under palladium-carbon to hydrogenate olefinic bonds, and debenzylation is performed to obtain 3,4,5-trimethoxy-3'-hydroxy-4'-ethoxydiphenyle-thane VII (hereinafter referred to as the code: ECB1);

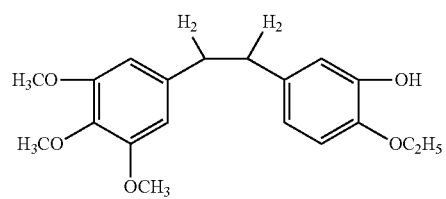

(6) the 3,4,5-trimethoxy-3'-hydoxy-4'-ethoxydiphenyle-thane (VII) is subjected to phosphorylation, phosphate esterification and sulfation to form ethoxyhydroxydiphenylethane water soluble derivative: disodium phosphate salt, sulfate salt, ammonium phosphate salt or choline phosphate inner salt.

(7) ECB1 forms 3,4,5-trimethoxy-4'-ethoxydiphenyle-thane-3'-o-disodium phosphate salt VII (hereinafter referred to as the code: ECB1P) under the action of phosphorylation agent phosphorus oxychloride and 2 mol/L of NaOH.

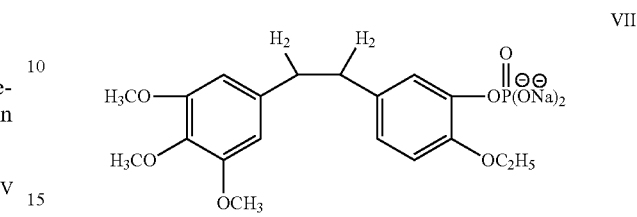

(8) another preferred phosphate esterification is characterized in that: ECB1 is reacted with dibenzyl phosphate to form benzyl phosphate, and sodium methoxide/absolute methanol is added under trimethylbromosilane (TMBS) to obtain 3,4,5-trimethoxy-4'-ethoxydiphenylethane-3'-o-disodium phosphate salt (hereinafter referred to as the code: ECB1P).

Another preferred embodiment of the invention provides a preparation method of aminoethoxydiphenylethylene in the compound of the formula (I), which comprises the steps that:

(1) Under phase transfer catalysis, 4-hydroxy-3-nitroben-zaldehyde IX is subjected to ethoxylation by bromethyl to form 4-ethoxy-3-nitrobenzaldehyde X;

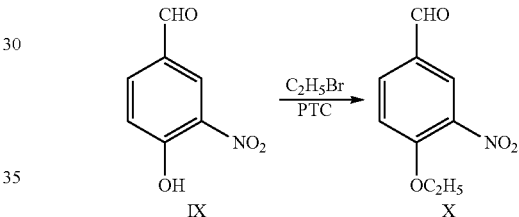

(2) trimethoxyphenyl bromide triphenylphosphonium methylide and the 4-ethoxy-3-nitrobenzaldehyde X are subjected to Wittig reaction to generate 3,4,5-trimethoxy-3'-nitryl-4'-ethoxydiphenylethylene XI;

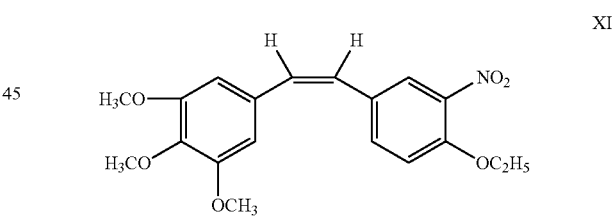

(3) the 3,4,5-trimethoxy-3'-nitryl-4'-ethoxydiphenylethyl-ene XI is subjected to hydrogenation reduction under palladium-carbon catalyst/sodium borohydride to reduce nitryl to amino and reduce olefinic bonds to ethane single bonds, so as to obtain 3,4,5-trimethoxy-3'-amino-4'-ethoxydiphenyle-thane XII (hereinafter referred as to the code: ECB1N)

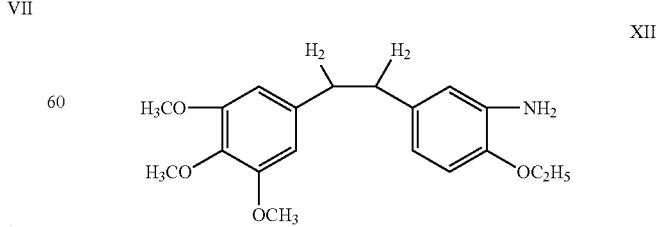

(4) the 3,4,5-trimethoxyl-3'-amino-4'-ethoxydiphenyle-thane (XII) and amino acid derivatives are subjected to reaction to form ethoxyaminodiphenylethane amino acid amide derivative having the amino acid amide side chain as below: natural amino acid side chain, or —NH(COCHR'NH)m-H (wherein R' is hydrogen, phenyl, and m represents an integer from 1 to 3).

(5) under the catalysis of dicyclohexylcarbo-diimide (DCC) and 1-hydroxybenzotrizole (HOBt) or hexafluorophosphatebenzotrizole-1-yl-oxo-tri(dimethylamino)phosphor(BOP agent), the 3,4,5-trimethoxy-3'-amino-4'-ethoxydiphenylethane XII is reacted with N-a-9-fluorenylmethoxycarbonyl amino acid derivative (Fmoc AA), amino at position 3' is converted into Fmoc-amino acid amide, Fmoc is removed to generate amino acid amides of ECB1N, which respectively are 3,4,5-trimethoxy-3'-glycylamino-4'-ethoxydiphenylethane XIII (hereinafter referred as to the code: ECB1GN) and 3,4,5-trimethoxy-3'-serylamino-4'-ethoxydiphenylethane XIV (hereinafter referred as to the code: ECB1SN)

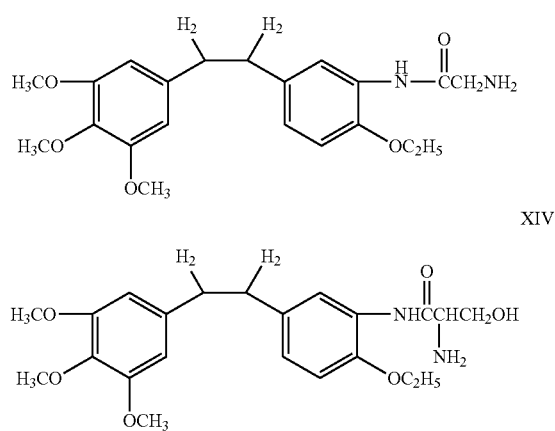

(6) the amino acid amide derivatives are dissolved in methanol, ethanol or isopropanol, and the equivalent amount of hydrochloric acid, sulfuric acid or phosphoric acid as well as petroleum ether or n-hexane are added to dilute the derivatives to form water soluble ammonium salt.

3. The pharmaceutical preparation of the invention is selected from the group consisting of the following forms: lyophiled powder, powder, injection, liposome, emulsion, micro-capsule, suspension or solution, administered in the form of intravenous injection; granule, tablet, capsule or syrup, administered orally; or suppository.

4. The use of the compound of the formula (I) in preparing tubulin aggregation inhibitor is provided.

5. The use of the compound of the formula (I) in preparing medicines having, as anti-tumor angiolysis agent, vascular target effect for various tumors is provided. The various tumors consist mainly of: lung cancer, non-small cell lung cancer, liver cancer, pancreatic cancer, gastric cancer, bone cancer, esophagus cancer, breast cancer, prostatic cancer, testicular cancer, colorectal cancer, ovarian cancer, bladder cancer, cervical cancer, melanoma, squamous cell carcinoma, basal cell carcinoma, adenocarcinoma, syringocarcinoma, carcinoma of sebaceous glands, papillary carcinoma, papillary adenocarcinoma, cystic adenoic carcinoma, cystocarcinoma, medullary cancer, bronchiolar carcinoma, bone cell carcinoma, epithelial carcinoma, cancer of biliary duct, choriocarcinoma, embryo carcinoma, spermatocytoma, embryonal adenomyosarcoma, spongiocytoma, astrocytoma, medulloblastoma, craniopharyngioma, ependymocytoma, pinealoma, hemocytoblastoma, vocal cord neuroma, meningoma, neuroblastoma, opticneuroblastoma, retinoblastoma, neurofibroma, fibrosarcoma, fibroblastoma, fibroma, fibroadenoma, fibrochondroma, fibrocystoma, fibromyxoma, fibro-osteoma, fibromyxosarcoma, fibropapilloma, myxosarcoma, myxocystoma, myxochondroma, myxochondrosarcoma, myxochondrofibrosarcoma, myxadenoma, myxoblastoma, liposarcoma, lipoma, lipoadenoma, lipoblastoma, lipochondroma, lipofibroma, lipoangioma, myxolioma, chondrosarcoma, chondroma, chondromyoma, notochordoma, chorioadenoma, chorionepithelioma, chorionic epithelioma, osteosarcoma, osteoblastoma, osteochondrofibroma, osteochondrosarcoma, osteochondroma, osteocystoma, osteodentinoma, fibroosteoma, fibrosarcoma of bone, angiosarcoma, hemangioma, angiolipoma, angiochondroma, angioblastoma, angiokeratoma, angioglioma, hemangiosarcoma, angiofibroma, angiomyoma, angiolipoma, hematolymphangioma, angiolipoleiomyoma, angiomyoliopma, angiomyoneuroma, angiomyxoma, angioreticuloendothelioma, lymphangiosarcoma, lymphogranuloma, lymphangioma, lymphadenoma, lymphomyxoma, lymphosarcoma, lymphangiofibroma, lymphocytoma, lymphoepithelioma, lymphoblastoma, endothelioma, endoblastoma, synovioma, synoviosarcoma, mesolepidoma, mesocytoma, Ewing's tumor, leiomyoma, leiomyosarcoma, leiomyoblastoma, leiomyofibroma, rhabdomyoma, rhabdomyosarcoma, rhabdomyomyxoma, acute lymphoblastic leukemia, acute myelocytic leukemia, chronic disease cytosis and erythrocytosis, lymphoma and multiple-myeloma.

6. The use of the compound of the formula (I) in preparing medicines for the treatment of diseases caused by abnormal angiogenesis is provided. The diseases mainly consist of: rheumatic arthritis, diabetic retinopathy, retinopathy of prematurity, retinal vein obstruction, psoriasis, rosacea, Kaposi's sarcoma, specific reaction keratitis, epidemic keratoconjunctivitis, neovascular glaucoma, bacterial ulcer, mycotic ulcer, simple herpesvirus infection, zoster herpesvirus infection, protozoal infection, mycobacterium infection, polyarteritis, sarcoid, sclerotitis, rubeosis, arthritis syndrome with symptoms of dry mouth and eyes, systemic lupus erythematosus, acquired immune deficiency syndrome and syphilis.

7. The drug effect, safety evaluation and positive controls of the compound of the formula (I) are as below:

(Z)-3,4,5-trimethoxy-3'-hydroxy-4'-methoxydiphenylethylene XV (hereinafter referred to as the code: CA4);

(Z)-3,4,5-trimethoxy-4'-methoxydiphenylethylene-3'-o-disodium phosphate salt XVI (hereinafter referred to as the code: CA4P);

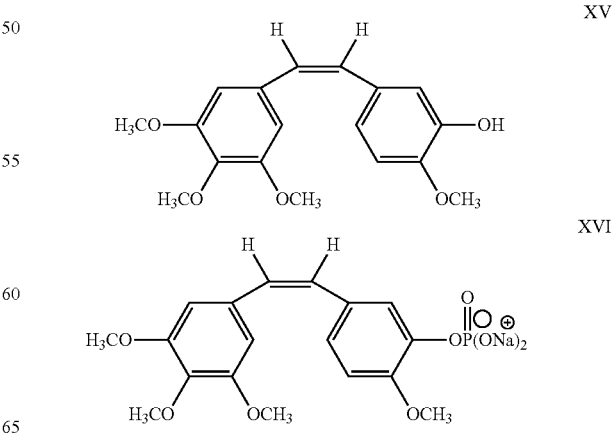

(Z)-3,4,5-trimethoxy-3'-amino-4'-methoxydiphenylethylene XVII (hereinafter referred to as the code: CA4N);

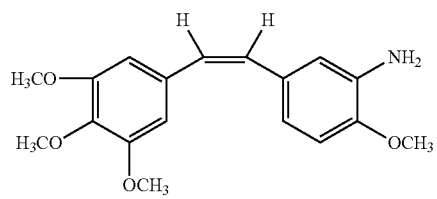

3,4,5-trimethoxy-3'-hydroxy-4'-methoxydiphenylethane XVIII (hereinafter referred to as the code: CB1)

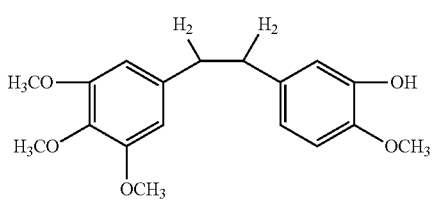

3,4,5-trimethoxy-4'-methoxydiphenylethane3'-o-disodium phosphate salt XIV (hereinafter referred to as the code: CB1P);

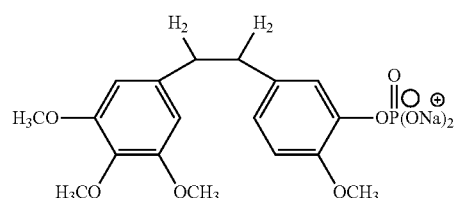

3,4,5-trimethoxy-3'-amino-4'-methoxydiphenylethane XX (hereinafter referred to as the code: CB1N)

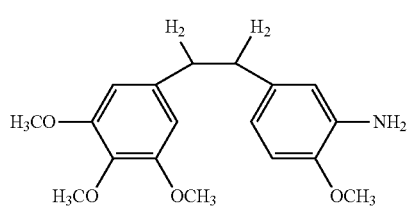

3,4,5-trimethoxy-3'-glycylamino-4'-ethoxydiphenylethane XXI (hereinafter referred to as the code: CB1GN)

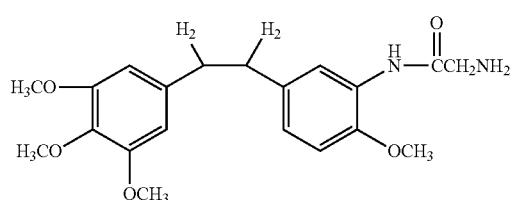

(Z)-3,4,5-trimethoxy-3'-hydroxy-4'-ethoxydiphenylethylene XXII (hereinafter referred to as the code: ECA4);

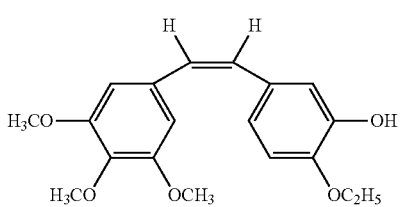

(Z)-3,4,5-trimethoxy-4'-ethoxydiphenylethylene-3'-o-disodium phosphate salt XXIII (hereinafter referred to as the code: ECA4P);

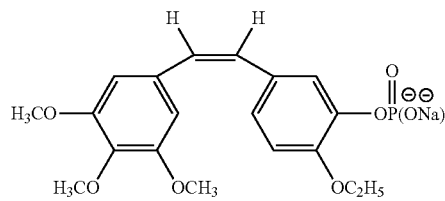

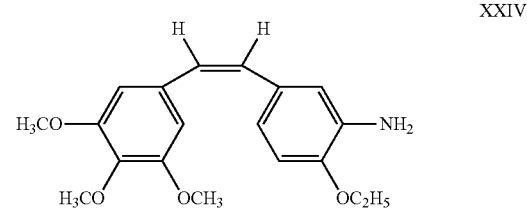

(Z)-3,4,5-trimethoxy-3'-amino-4'-ethoxydiphenylethylene XXIV (hereinafter referred to as the code: ECA4N);

(Z)-3,4,5-trimethoxy-3'-glycylamino-4'-ethoxydiphenylethane XXV (hereinafter referred to as the code: ECA4GN)

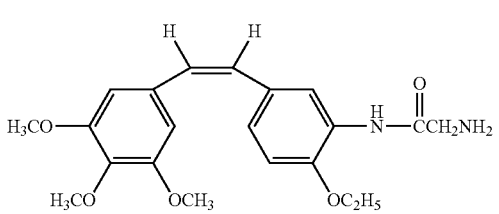

8. The drug effect and the safety evaluation results of the compound of the formula (I) are concluded as below:

(1) the result of the antitumor activity evaluation for in vitro cultured tumor cells shows that, by comparison, position 4' ethoxydiphenylethane compounds ECB1 and ECB1N as well as position 4' ethoxydiphenylethylene positive control compounds ECA4 and ECA4N have obvious and basically equivalent antitumor activities for multiple in vitro cultured tumor cells, the antitumor activities thereof are prominently stronger than those of position 4' methoxy positive control compounds CA4, CB1 and CB1N (about 10 to 200 times), and as for colorectal cancer HT-29, ECB1N is about 200 times stronger than position 4' methoxy positive control CB1 and ECB1 is about 100 times stronger than positive control CB1.

(2) the growth of solid tumors depends on vascular system, a part of tumor vascular endothelial cells under rapid proliferation depend more on microtubule to maintain intact structure owing to the shortage of intact myofilament structures, the rapid proliferation of proliferous human umbilical vein endothelial cells (HUVEC) depends more on microtubule to maintain intact structure, so the microtubule is usually used as in vitro model for tumor vascular endothelial cells and the human umbilical vein endothelial cells (HUVEC) are used as action objects in order to evaluate the anti-tumor vessel property of ethoxydiphenylethane derivatives, ethoxydiphenylethane derivative ECB1N with the $IC_{50}$ of $6.8 \times 10^{-4}$ μmol/L and ethoxydiphenylethane derivative ECB1 with the $IC_{50}$ of $7.5 \times 10^{-4}$ μmol/L have the proliferation inhibiting effect for human umbilical vein endothelial cells, so a tubulin aggregation inhibitor which is quite obviously stronger than position 4' methoxy positive control compounds CA4, CB1 and CB1N (with the $IC_{50}$ ranging from $4.8\times10^{-3}$ to $7.7\times10^{-3}$) is shown, indicating that the ethoxydiphenylethane derivative is a potential, quite strong tumor vascular target drug.

(3) the result of the tumor-inhibiting rate experiment of in vivo intravenous injection tested drugs to S180 sarcoma transplanted tumor in mice shows that, according to the administration proposal, all the tested compounds can obviously inhibit the growth of S180 sarcoma transplanted tumor in mice, and it is observable around the eighth day after drug administration that, by comparison, position 4' ethoxydiphenylethane derivatives ECB1P. ECB1GN hydrochloride and ECB1SN hydrochloride as well as position 4' ethoxydiphenylethylene positive control compounds ECA4P and ECA4GN hydrochloride both achieve the tendency of tumor shrinkage in drug administered group, reach over 60% of the tumor inhibiting rate in case of 50 mg/kg dose and have fundamentally equivalent therapeutic effects, which are obviously superior to the therapeutic effects, i.e. about 40% of the tumor inhibiting rate, of methoxy positive controls CB1GN hydrochloride, CB1P and CA4P in case of 100 mg/kg dose.

(4) in the acute toxicity test of single mice intraperitoneal injection administration, high-dose injection administration causes the death of mice 40 minutes and 1 hour later, obvious residual liquid is not found after dissection, indicating the fast absorption of the drugs, and the other mice mainly die 1 to 2 days after the administration, no death of mice is observed after the fifth day, no abnormality of the heart, lung, liver, spleen, kidney and other organs in dead mice is found through dissection, and the surviving mice suffer from diarrhea not severe, which indicates that the tested drugs mainly lead to acute toxic response without obvious delayed toxicity, therefore, the result of the test shows that ethoxydiphenylethane compounds ECB1P, ECB1GN hydrochloride and ECB1SN hydrochloride have the toxicity lower than ethoxydiphenylethylene positive control compounds ECA4P and ECA4GN hydrochloride in administration group.

9. The research of the invention has found that ethoxydiphenylethane compounds, i.e. the compounds of the formula (I), can form active target with hydroxy and amino at position 3' by modifying original methoxy at diphenylethane B aromatic ring position 4' into ethoxy, and can greatly enhance the tumor vascular target activity thereof compared with methoxydiphenylethane compounds with original methoxy at B aromatic ring position 4' and hydroxy and amino at position 3'; the experiment shows that position 4' ethoxydiphenylethane compounds ECB1 and ECB1N both have obvious antitumor activity for multiple in vitro cultured tumor cells and are prominently stronger than position 4' ethoxy positive control compounds CA4. CB1 and CB1N (10 to 200 times), and as for colorectal cancer HT-29. ECB1N is about 200 times stronger than positive control CB1, and ECB1 is about 100 times stronger than positive control CB1.

Two benzene rings are connected through single bonds so that the compound has the structure, conformation, bonding force and reversal effect different from diphenylethylene compound CombretastatinA-4, in addition, no cis-trans configuration difference exists, drug stability can be greatly raised while toxicity can be lowered, preparation technology can be better simplified, no column chromatography separation is required, technological yield is prominently enhanced, consumption of raw materials is considerably reduced, technological cost of unit synthesis is also tremendously lowered, drug stability is raised, storage away from light is not required so as to bring great convenience for storage and actual application, and unexpected effects are obtained.

DETAILED DESCRIPTION OF EMBODIMENTS

Figure 1:
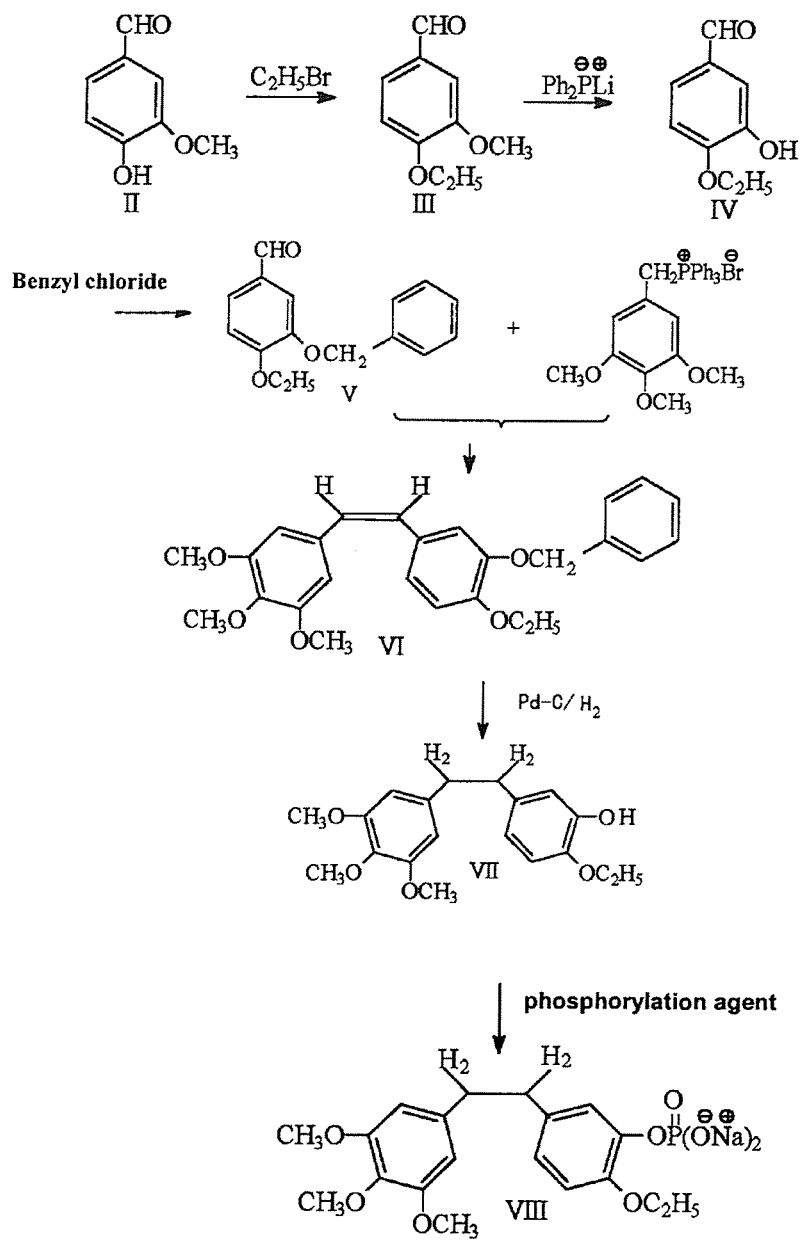
FIG. 1: a synthetic route of hydroxyethoxydiphenylethane compound and the water soluble prodrug thereof.
Figure 2:
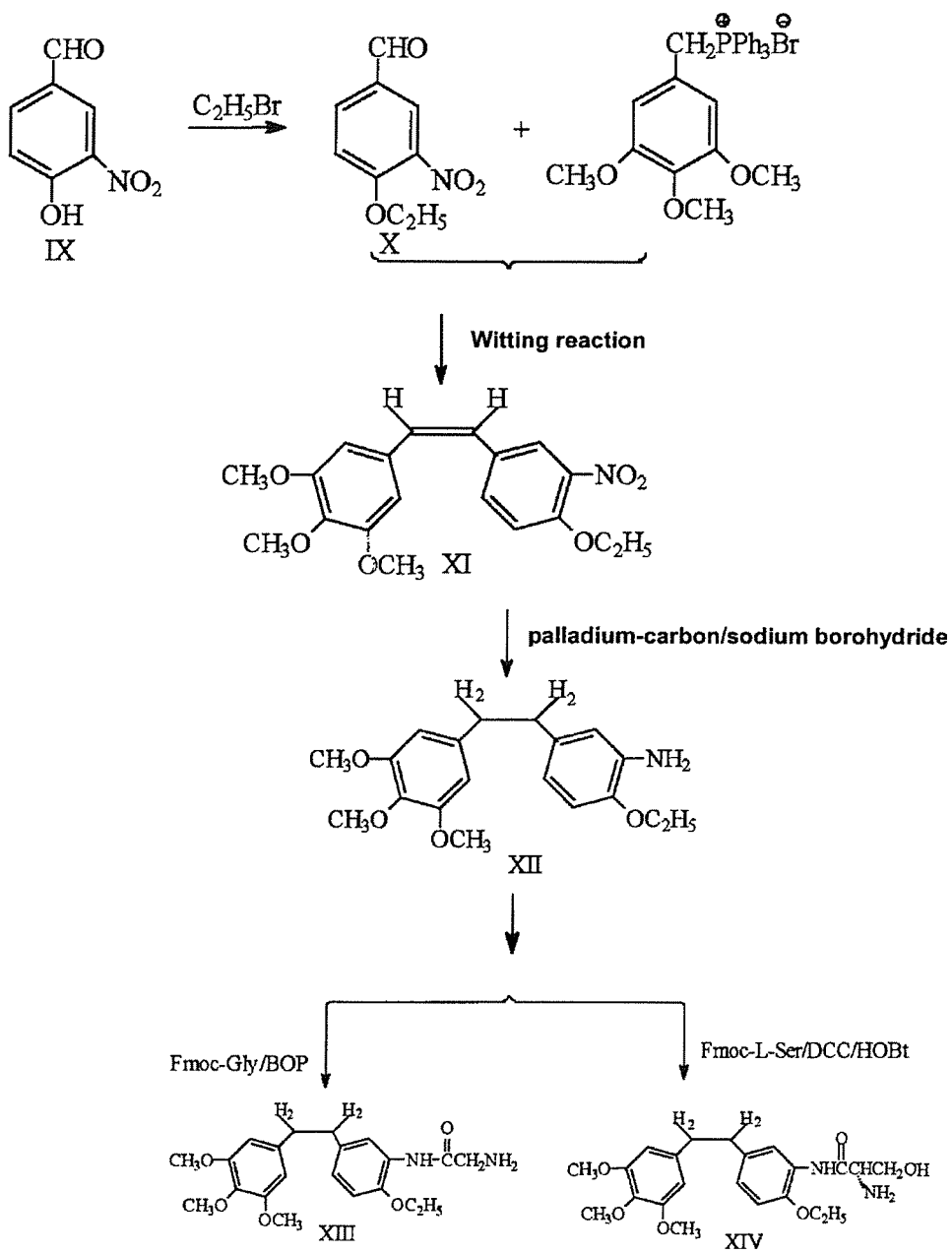
FIG. 2: a synthetic route of aminoethoxydiphenylethane compound and the amino acid amide derivative thereof.

Embodiment 1:

Preparation of 4-ethoxy-3-methoxybenzaldehyde 76 grams of 4-hydroxy-3-methoxybenzaldehyde (0.5 mol) and 500 mL of isopropanol are added into a four-necked flask and then stirred for 20 minutes, a constant pressure dropping funnel is used for slowly dropping 150 milliliters of aqueous solution of 6.5 grams of 18-crown-6 ether and 133 grams of sodium hydroxide, and stirring is performed for 30 minutes, the reaction system is heated to 60° C., at which 85 grams of bromethyl is dropped for reacting for 5 to 6 hours while TLC tracking is implemented, after the reaction ends, the reaction system is cooled (to 15° C.) and is added with 500 mL of water for stopped reaction, the product is extracted by ether (3×300 mL), organic phase is washed with water to be neutral, anhydrous $MgSO_4$ is dried, ether is partially distilled, a large amount of petroleum ether is added to precipitate crude product, the crude product is subjected to recrystallization by ether/petroleum ether to obtain 83 grams of 4-ethoxy-3-methoxybenzaldehyde:, and the yield is 92%.

Embodiment 2:

Preparation of 4-ethoxy-3-hydroxybenzaldehyde

Step 1: under the protection of argon, 54 grams of 4-ethoxy-3-methoxybenzaldehyde (0.3 mol) is added to a three-necked flask which is then added with 130 grams of ethylene glycol (2.1 mol) and 133 grams of diethyl orthoforniate (0.9 mol) for reflux at about 100 ° C., and 1 ml of boron trifluoride ether solution is added as catalytst. Reaction is performed for 24 hours while TLC tracking is implemented, the reaction product is cooled to room temperature and added with 200 ml of 15% aqueous sodium hydroxide solution, followed by extraction with 300 ml of ether, washing with saturated saline solution and drying with anhydrous magnesium sulfate, and yellow oily matters are obtained by means of reduced pressure distillation of ethylene glycol and Methyl orthoformate.

Step 2: 56 grams of acetal (0.25 mol) is added in batches to 200 ml of 1.28M lithium diphenylphosphide tetrahydrofuran solution, stirring at room temperature is performed for 3 to 4 hours while TLC tracking is implemented, water is added for stopped reaction, the reaction product is added with 200 ml of 30% sodium hydroxide solution and than extracted with 300 ml of ether, acidified with hydrochloric acid, pH-adjusted to about 3 to 4 and finally extracted with 500 ml of ether, ether extract liquids are merged, washed with water and saturated saline solution, dried with anhydrous magnesium sulfate and filtered, yellow solids are obtained by means of reduced pressure removal of solvent and then subjected to recrystallization by benzene/petroleum ether to obtain 38.1 grams of yellowish crystals, and the yield is 76%.

Embodiment 3

Preparation of 4-ethoxy-3-benzyloxybenzaldehyde 16.6 grams of 4-ethoxy-3-hydroxybenzaldehyde (100 mmol.) and 200 ml of absolute ethyl alcohol are added to a three-necked flask and then heated to 40° C. for being dissolved, 9 grams of potassium carbonate (65.07 mmol.) is added, 15 ml of benzyl chloride (130.13 mmol.) is added under stirring, heating reflux is performed for 1 hour, the reaction product is cooled to 50° C. after complete reaction is detected by TLC and then filtered while it is hot, the filtrate is put in a refrigerator for being cooled over night, crystals are separated out and pump-filtered, filter cakes are washed with 30 mL of absolute ethyl alcohol and then vacuum-dried to obtain 21.5 grams of white needle crystals, and the yield is 83.9%.

Embodiment 4

Preparation of 3,4,5-trimethoxy-3'-benzyloxy-4'-ethoxydiphenylethylene

A three-necked bottle is added with 20 grams of 3,4,5-trimethoxy trimethoxy biphenyl benzylidene bromide phosphonium bromide and 150 ml of tetrahydrofuran, suspension is stirred so that 10.5 g 4-ethoxy-3-benzyloxybenzaldehyde (41.0 mmol.) is dissolved in 70 ml of tetrahydrofuran, and the tetrahydrofuran is put in a dropping funnel with the capacity of 100 ml. A reaction flask is added with 7.5 grams of solid potassium tert-butoxide (66.5 mmol.), the reaction system is changed into sanguine, stirring at room temperature is performed for 5 minutes, the solution of 4-ethoxy-3-benzyloxybenzaldehyde is slowly dropped, stirring at room temperature is performed once again for 20 minutes, the reaction product is poured into a separating funnel with the capacity of 500 ml after complete reaction is detected by TLC, the solution is layered after being added with 140 ml of deionized water, followed by the addition of 300 ml×2 of ether for extraction, merging of ether layers, drying with anhydrous magnesium sulfate and filtration, filter cakes are washed with 50 mL of ether, the filtrate is dried by a rotary evaporator through concentration in order to obtain 25 grams of oily matters, the oily matters are added with 20 mL of absolute ethyl alcohol and then pump-filtered to obtain 14.1 grams of yellowish solids, the yellowish solids are put in a round bottom flask and added with 25 ml of absolute ethyl alcohol, followed by dissolution of partial solids by means of heating, stirring at room temperature and pump filtration, filter cakes are washed with 10 ml of absolute ethyl alcohol and then dried by an infrared lamp to obtain 10.6 grams of pure 3,4,5-trimethoxy-3'-benzyloxy-4'-ethoxydiphenylethylene, i.e. yellowish powdery solids, and the yield is 61.6%.

Embodiment 5

Preparation of 3,4,5-trimethoxy-3'-hydroxy-4'-ethoxydiphenylethane (Hereinafter Referred to as the Code: ECB1)

Step 1: 10.6 grams of pure 3,4,5-trimethoxy-3'-benzyloxy-4'-ethoxydiphenylethylene (25.8 mmol.) is added into a three-necked flask and dissolved in 200 ml of ethyl acetate and 120 ml of absolute ethyl alcohol, the resultant yellowish solution is added with 1.0 gram of 5% palladium carbon, hydrogen is fed in under stirring, the solution is stirred at room temperature for 1 hour and filtered to obtain anhydrous solution, the anhydrous solution is dried by a rotatory evaporator through concentration in order to obtain 8.06 grams of oily matters, i.e. the crude product of 3,4,5-trimethoxy-3'-hydroxy-4'-ethoxydiphenylethane, and the yield is 96.8%.

Step 2: 8.06 grams of the crude product of 3,4,5-trimethoxy-3'-hydroxy-4'-ethoxydiphenylethane is added into a round bottom flask and dissolved in 40 ml of absolute ethyl alcohol, insolubles are removed by filtration in case of the presence thereof, the solution stands still at room temperature while crystals are separated out and stands over night to completely volatilize solvent, and white crystals in large quantities are separated out. The white crystals are filtered, filter cakes are washed with ethanol to obtain 6.7 grams of white crystals, and the yield is 83%.

Embodiment 6

Preparation (Phosphate Esterification 1) of 3,4,5-trimethoxy-4'-ethoxydiphenylethane-3'-o-disodium phosphate salt (Hereinafter Referred to as the Code: ECB1P)

A round bottom flash is added with 4.4 ml of phosphorus oxychloride (47.4 mmol.) and 25 ml of dichloromethane, the solution resulted from 5 grams of 3, 4, 5-trimethoxy-3'-hydroxy-4'-ethoxydiphenylethane (15.1 mmol.) in 10 ml of dichloromethane is dropped and stirring is then performed for 5 minutes, the solution resulted from 3.3 ml of triethylamine (23.8 mmol.) in 5 ml of dichloromethane is dropped, followed by stirring at room temperature for 3 hours and TLC detection, and 100 ml of cold water is added for quenching subsequent to complete reaction. Organic phase is separated out by means of sufficient oscillation and washed with 50 mL×2 of water, organic layers are merged after aqueous layer is extracted by dichloromethane, dried over night with a proper amount of anhydrous sodium sulfate and pump-filtered, the filtrate is subjected to reduced pressure distillation to remove thick liquid of solvent, and under the cooling of ice bath, 2 mol/L of NaOH solution is added under stirring until the pH of mixed solution reaches the range from 8 to 10, stirring is performed at 65° C. for 8 hours, insolubles are removed by filtration, the majority of the solution is subjected to reduced pressure distillation, crystals are separated out by cooling to obtain white solids, i.e. the crude product of 3,4,5-trimethoxy-4'-ethoxydiphenylethane-3'-o-disodium phosphate salt, the crude product is dissolved in ethanol by means of heating, the product-dissolved ethanol is filtered while it is hot to remove insoluble solids, the filtrate is cooled to separate out crystals in order to obtain about 5.6 grams of white crystallized product, i.e. the pure product, and the yield is 81.6%.

$^1$H-NMR (ppm) δ: 7.33 (d, 1H, 2' -H); 6.89 (d, 1H, 6' -H); 6.67 (d, 1H, 5-H); 6.58 (s, 2H, 2, 6-H); 4.18 (2H, q; —OCH2); 3.80(s, 3H, 4-OCH$_3$); 3.76(s, 6H, 3, 5-OCH$_3$); 2.82(d, 1H, J=13.2 Hz, Ia-H); 2.79 (d, 1H, J=13.3 Hz, Ia'-H); 1.52 (3H, t;-CH$_3$)

$^{13}$C NMR (ppm) δ: 14.9, 37.8, 38.2, 56.1, 56.3, 64.7, 105.3, 114.3, 115.2, 138.4, 121.6, 132.2, 133.8, 145.0, 150.1, 136.7

Embodiment 7

Preparation (Phosphate Esterification 2) of 3,4,5-trimethoxy-4'-ethoxydiphenylethane-3'-o-disodium phosphate salt (Hereinafter Referred to as the Code: ECB1P)

Step 1: under the atmosphere of argon, 4.2 grams of 3,4,5-trimethoxy-3'-hydroxy-4'-ethoxydiphenylethane (12.6 mmol.) is added into a four-necked flask and is then dissolved with 40 mL of dry acetonitrile and cooled to −2.5° C., 6 ml of carbon tetrachloride is then added, 4.7 ml of diisopropylethylamine and 0.15 grams of 4-dimethylaminopyridine are added after stirring is continuously stirred for 5 minutes, 1 minute later, 4 ml of dibenzyl phosphate (80%) is slowly added, the temperature is kept below −10° C., reaction is continuously performed for 3.5 hours while TLC tracking is implemented, 10 m of 10.5M $KH_2PO_4$ is added upon complete reaction, followed by natural rise of the temperature to room temperature, extraction with ethyl acetate, merging of organic layers, sequential washing with distilled water and saturated saline water, drying with anhydrous magnesium sulfate and reduced pressure distillation of solvent to obtain muddy oily matters, the oily matters are subjected to recrystallization by ethyl acetate-n-hexane to obtain 6.6 grams of colorless needle crystals, and the yield is 88%.

Step 2: 6.5 grams of the resultant dry benzyl phosphate (10.8 mmol.) is added into a four-necked flask and is dissolved with 25 ml of dry anhydrous acetonitrile, stirring is performed at 15° C. under the atmosphere of argon, 4.5 ml of trimethylbromosilane (TMBS) is rapidly dropped, 7 ml of absolute methanol solution containing 1.8 grams of sodium methoxide is added 5 and 10 minutes later so that the reaction system is immediately changed into suspension in milky white, 3.6 ml of absolute methanol and 3.6 ml of acetone are added half an hour later, the suspension stands over night under stirring and is then pump-filtered to obtain white solids, the white solids are washed with absolute methanol and acetone and than dried in vacuum. 4.1 grams of white powders are obtained by means of recrystallization by water/methanol/acetone, and the yield is 83.6%.

1H-NMR (ppm) δ: 7.34 (d, 1H, 2' -H); 6.88 (d, 1H, 6' -H); 6.68 (d, 1H, 5'-H); 6.60 (s, 2H, 2, 6-H); 4.20 (2H, q; —$OCH_2$); 3.76(s, 3H, 4-$OCH_3$); 3.75(s, 6H, 3, 5-$OCH_3$); 2.81(d, 1H, J=13.6 Hz, Ia-H); 2.79 (d, 1H, J=13.6 Hz, Ia'-H); 1.54 (3H, t;-$CH_3$)

$^{13}C$ NMR(ppm) δ: 14.8, 37.8, 38.3, 56.1, 56.3, 64.6, 105.5, 114.6, 115.3, 138.3, 121.7, 132.4, 133.8, 145.1, 150.1, 136.7

Embodiment 8:

Preparation of 4-ethoxy-3-nitrobenzaldehyde 83.5 grams of 4-hydroxy-3-nitrobenzaldehyde (0.5 mol), 668 mL of N. N-dimethyl formamide, 167 grams of potassium carbonate and 8.35 grams of 18-crown-6 ether are added into a four-necked flask and stirred at the temperature ranging from 55 to 65° C., about 80 grams of bromethyl is then added for reaction for 5 to 6 hours while TLC tracking is implemented, the reaction product is cooled to 40° C. upon the ending of the reaction and added with 600 ml of purified water for stopped reaction, the reaction product is extracted with ether (3×300 mL), organic phase is washed with water to be neutral, followed by drying with anhydrous $MgSO_4$, distillation of partial ether and addition of petroleum ether in larger quantities to precipitate the crude production, the crude product is subjected to recrystallization by ether/petroleum ether to obtain 80.9 grams of 4-ethoxy-3-nitrobenzaldehyde, and the yield is 83%.

Embodiment 9

Preparation of 3,4,5-trimethoxyphenyl-3'-nitryl-4'-ethoxydiphenylethylene

Under the protection of argon, 15 grams of trimethoxyphenyl bromide triphenylphosphonium methylide (28.7 mmol.) is suspended in 300 ml of THF with the temperature being cooled to about −15° C. 22 ml of n-butyllithium cyclohexane solution (1.6 mol/L) is dropped for reaction for 1 hour. 24 ml of THF solution containing 5.7 grams of 4-ethoxy-3-nitrobenzaldehyde (29 mmol.) is slowly dropped into the reaction while TLC tracking is implemented, followed by stirring over night and rise of the reaction temperature to room temperature, the temperature of the solution is cooled to −5° C., saturated saline water is added for stopped reaction, organic layers are separated, ¾ of the solvent is removed, absolute ethyl alcohol 4 times as much as the rest mother solution is added for recrystallization at the temperature ranging from 0 to −5° C., 6.8 grams of yellowish matters are obtained by means of filtration, and the yield is 65%.

Embodiment 10

Preparation of 3,4,5-trimethoxy-3'-amino-4'-ethoxy-diphenylethane (Hereinafter Referred as to the Code: ECB1N)

100 ml of water, 0.5 grams of 10% palladium carbon catalyst and the solution resulted from 8 grams of sodium borohydride dissolved in 150 ml of water are added into a reaction flask, nitrogen is fed in the reaction flask, 6.8 grams of 3, 4, 5-trimethoxy-3'-nitryl-4'-ethoxydiphenylethylene (16.6 mmol) is dropped under stirring to be dissolved in 2 mol/L of solution resulted from 250 ml of NaOH, the dropping process lasts about 20 minutes, the solution is then filtered, the filtrate is acidified with 2 mol/L of HCL to decompose excessive sodium borohydride, is then neutralized with diluted NaOH and finally extracted with ether (100 ml×4), ether extract liquids are merged and dried with anhydrous magnesium sulfate to distill ether, 4.8 grams of colorless crystals are obtained by means of recrystallization by n-hexane/ethyl acetate according to the ratio of about 9:1, and the yield is 83%.

$^1$H-NMR (ppm) δ: 7.14 (d, 1H, 2' -H); 6.88 (d, 1H, 6' -H); 6.68 (d, 1H, 5'-H); 6.60 (s, 2H, 2, 6-H); 448(brs, 2H, $NH_2$); 4.08(q, 2H,—$CH_2$); 3.77(s, 3H, 4-$OCH_3$); 3.75(s, 6H, 3, 5-$OCH_3$); 2.85(d, 1H , J=12.5 Hz, Ia-H); 2.78 (d, 1H, J=12.5 Hz, Ia'-H); 1.56 (3H, t; —$CH_3$).

MS (m/Z):331 ($M^+$); high-resolution mass spectrometry, calculated value: 331.1784, measured value: 331.1753.

Embodiment 11

Preparation of 3,4,5-trimethoxy-3'-glycylamino-4'-ethoxydiphenylethane XIII (Hereinafter Referred as to the Code: ECB1(SN)

Step 1: 4.8 grams of 3,4,5-trimethoxy-3 -amino-4'-ethoxy-diphenylethane (14.5 mmol), 5.27 grams of Fmoc-glycine (17.8 mmol) and 25 grams of BOP reagent are dissolved in 100 ml of DMF, the reaction mixture is heated up 60° C. under stirring and subjected to reaction for 2 hours while TLC tracking is implemented, the reaction product is cooled upon the ending of the reaction and added with 100 ml of saturated sodium bicarbonate solution for being uniformly mixed. The mixture is extracted with 120 ml×3 of dichloromethane, organic layers are dried with anhydrous magnesium sulfate, 6.6 grams of white matters are obtained by means of reduced pressure concentration, and the yield is 75%.

Step 2: 6.6 grams of the above resultant 3,4,5-trimethoxyphenyl-3'-amino-4'-ethoxydiphenylethane-Fmoc-glycineamide (10.8 mmol) is dissolved in 120 ml of methanol, the methanol is then added with 6 ml of 2N sodium hydroxide solution under stirring for reaction for 3 hours while TLC tracking is implemented, the reaction product is cooled upon the ending of the reaction and added with 60 ml of saturated sodium bicarbonate solution for being uniformly mixed, the mixture is extracted with 150 ml×3 of dichloromethane, organic layers are dried with anhydrous magnesium sulfate, 3.2 grams of white powdery matters are obtained by means of filtration at first and then reduced pressure concentration, and the yield is 77%.

1H-NMR (CDCl$_3$, 500M)δ: 9.54 (brs, 1H, —NH); 7.04 (d, 1H, 2'-H); 6.92 (d, 1H, 6'-H); 6.78 (d, 1H, 5'-H); 6.65 (s, 2H, 2, 6-H); 4.77 (brs, 2H, Cly-NH$_2$); 4.20 (brs, 2H, G1 y-CH$_2$); 4.02 (q, 2H,—CH$_2$); 3.76 (s, 3H, 4-OCH$_3$); 3.75(s, 6H, 3, 5-OCH$_3$); 2.88 (d, 1H, J=12.8 Hz, Ia-H); 2.78 (d, 1H, J=12.8 Hz, Ia'-H); 1.55 (3H, t; —CH$_3$).

MS (m/Z):338 (M$^+$); high-resolution mass spectrometry, calculated value: 338.1998, measured value: 338.1945.

Embodiment 12

Preparation of 3,4,5-trimethoxy-3'-serylamino-4'-ethoxydiphenylethane (Hereinafter Referred as to the Code: ECB1SN)

Step 1: 4.8 grams of 3,4,5-trimethoxy-3'-amino-4'-ethoxydiphenylethane (14.5 mmol), 6.5 grams of Fmoc-serine (17.8 mmol), 3.7 grams of DCC (dicyclohexylcarbo-diimide) (17.8 mmol) and 2.7 grams of HOBt (1-hydroxy-benzo-triazole) are dissolved in 90 ml of DMF, the reaction mixture is subjected to reaction under stirring at room temperature for 5 hours while TLC tracking is implemented, the reaction product is cooled upon the ending of the reaction and added with 60 ml of ethyl acetate for being uniformly mixed, the mixture is filtered and dried with anhydrous magnesium sulfate, 6.5 grams of white matters are obtained by means of reduced pressure concentration, and the yield is 74%.

Step 2: 6.5 grams of the above resultant matters are dissolved in the mixed solvent of 70 ml of methanol and 70 ml of dichloromethane, the mixed solvent is added with 12 ml of 2N sodium hydroxide solution under stirring for reaction at room temperature for 24 hours while TLC tracking is implemented, the reaction product is cooled upon the ending of the reaction and added with 670 ml of saturated sodium bicarbonate solution for being uniformly mixed, the mixture is extracted with 150 ml×3 of dichloromethane, organic layers are dried with anhydrous magnesium sulfate, 3.3 grams of white powdery matters are obtained by means of filtration at first and then reduced pressure concentration, and the yield is 79%.

$^1$H-NMR (CDCl$_3$, 500M)δ: 9.65 (brs, 1H, —NH); 7.06 (d, 1H, 2'-H); 6.90 (d, 1H, 6'-H); 6.76 (d, 1H, 5'-H); 6.66 (s, 2H, 2, 6-H); 5.27 (brs, 2H, Ser-NH$_2$); 4.50 (brs, 2H, Ser-OH); 4.19 (q, 2H,—CH$_2$); 3.93 (m,1H,Ser-CH); 3.86(s, 3H, 4-OCH3); 3.80 (s, 6H, 3, 5-OCH$_3$); 2.92 (d, 1H, J=13.2 Hz, Ia-H); 2.85 (d, 1H, J=13.2 Hz, Ia'-H); 2.67 (m, 2H, Ser-CH$_2$); 1.54 (3H, t;—CH$_3$).

MS (m/Z):418 (M$^+$); high-resolution mass spectrometry, calculated value: 418.2104, measured value: 418.2114.

Embodiment 13 (Antitumor Activity Evaluation for In Vitro Cultured Tumor Cells)

1. Test Method

Cells are cultured with RPMI 1640 culture solution containing 200 mL/L of fetal bovine serum to be constantly in logarithmic phase, and are inoculated to a 96-well plate at the density of 4 to 8×10$^4$/ml (HUVEC density is 3×10$^4$/mL), administration with the drugs having 6 concentrations is continuously given at 37° C. for 48 hours in case of 3 duplex wells for each drug 24 hours after preculture, the culture solution is separated and air-dried, each well is added with 50 μL of cold trichloroacetic acid with the concentration of 500 g/L (final concentration thereof is 100 g/L), followed by fixation for 60 minutes, then washing with deionized water 4 to 5 times and finally drying, each well is added with 100 μL of SRB with the concentration of 4 g/L for effecting for 30 minutes, followed by soft washing with 10 ml/L of acetic acid four times and drying, each well is added with 200 μL of Tris base (10 mmol) for uniform shaking and mixing and is subjected to oscillation for 5 minutes on a flat oscillator, value A is determined by an enzyme linked immunosorbent assay reader and is zero-set by blank control at the wavelength of 490 nm, the tumor inhibiting rate (%)=(average value of drug-free cell control well value A−average value of drug-applied well value A)/ (average value of drug-free cell control well value A×100%), the positive controls are CA4, CB1 and CB1N, and based on Logit method, the IC$_{50}$ is calculated according to the cell growth inhibiting rates of drugs under different concentrations.

2. Test Results:

By comparison, position 4' ethoxydiphenylethane compounds ECB1 and ECB1N as well as position 4' ethoxydiphenylethylene positive control compounds ECA4 and ECA4N have obvious and basically equivalent antitumor activities for multiple in vitro cultured tumor cells, the antitumor activities thereof are prominently stronger than those of position 4' methoxy positive control compounds CA4, CB1 and CB1N (about 10 to 200 times), and as for colorectal cancer HT-29, ECB1N is about 200 times stronger than CB1 and ECB1 is about 100 times stronger than CB1.

The growth of solid tumors depends on vascular system, a part of tumor vascular endothelial cells under rapid proliferation depend more on microtubule to maintain intact structure owing to the shortage of intact myofilament structures, the rapid proliferation of proliferous human umbilical vein endothelial cells (HUVEC) depends more on microtubule to maintain intact structure, so the microtubule is usually used as in vitro model for tumor vascular endothelial cells and the human umbilical vein endothelial cells (HUVEC) are used as action objects in order to evaluate the anti-tumor vessel property of ethoxydiphenylethane derivatives, ethoxydiphenylethane derivative ECB1N with the IC$_{50}$ of 6.8×10$^{-4}$ μmol/L and ethoxydiphenylethane derivative ECB1 with the IC$_{50}$ of 7.5×10$^{-4}$ μmol/L have the proliferation inhibiting effect for human umbilical vein endothelial cells, which is obviously stronger than position 4' methoxy positive control compounds CA4. CB1 and CB1N (with the IC$_{50}$ ranging from 4.8×10$^{-3}$ to 7.7×10$^{-3}$), indicating that the ethoxydiphenylethane derivative is a potential, quite strong tumor vascular target drug.

Determination Result of Antitumor Activity Evaluation for in vitro Cultured Tumor Cells

| Tumor | IC$_{50}$ (μmol/L) | | | | | | |
|---|---|---|---|---|---|---|---|
| | CA4 | CB1 | CB1N | ECA4 | ECA4N | ECB1 | ECB1N |
| Human colorectal cancer cell HT-29 | 2.1 × 10$^{-2}$ | 3.5 × 10$^{-2}$ | 3.9 × 10$^{-2}$ | 2.8 × 10$^{-4}$ | 1.5 × 10$^{-4}$ | 3.4 × 10$^{-4}$ | 1.8 × 10$^{-4}$ |
| Non-small cell lung cancer cell NCl-H292, | 2.4 | 2.8 | 3.0 | 0.16 | 0.10 | 0.17 | 0.12 |

-continued

| Tumor | IC$_{50}$ (μmol/L) | | | | | | |
|---|---|---|---|---|---|---|---|
| | CA4 | CB1 | CB1N | ECA4 | ECA4N | ECB1 | ECB1N |
| Gastric cancer SGC-7901 | $3.6 \times 10^{-3}$ | $4.2 \times 10^{-3}$ | $4.8 \times 10^{-3}$ | $2.5 \times 10^{-4}$ | $1.9 \times 10^{-4}$ | $2.8 \times 10^{-4}$ | $1.5 \times 10^{-4}$ |
| Liver cancer Bel-7402 | 0.83 | 1.7 | 2.5 | $6.3 \times 10^{-2}$ | $3.9 \times 10^{-2}$ | $5.7 \times 10^{-2}$ | $3.4 \times 10^{-2}$ |
| Human umbilical vein endothelial cell (HUVEC) | $4.8 \times 10^{-3}$ | $5.6 \times 10^{-3}$ | $7.7 \times 10^{-3}$ | $8.0 \times 10^{-4}$ | $7.6 \times 10^{-4}$ | $7.5 \times 10^{-4}$ | $6.8 \times 10^{-4}$ |

Embodiment 14 (Tumor-inhibiting Rate Experiment of in vivo Intravenous Injection Tested Drugs to S180 Sarcoma Transplanted Tumor in Mice)

1. Experimental Method:

After 1 week for adaptation, mice are subcutaneously inoculated with S180 sarcoma tissues and randomly grouped after the tumor grows as much as the area of 100 to 300 mm³; every compound is used for 6 mice in drug administered group and for 12 mice in control group, the administration doses are as below: 25, 50 mg/kg of ECB1P, ECB1GN hydrochloride, ECB1SN hydrochloride and positive controls ECA4P, ECA4GN hydrochloride, as well as 50, 100 mg/kg of positive controls CB1GA hydrochloride, CB1P and CA4P, the administration is given intravenously on Day d0, d2, d4, d6, d8, d10 and d12, seven times in total, measurement of tumor volume, mice weighing and data recording are performed three times every week, the mice are executed on the fourteenth day after inoculation, tumor tissues are weighed to calculate the tumor-inhibiting rate, tumor weight inhibiting rate %=(1−average tumor weight in treatment group/average tumor weight in control group)×100%.

2. Experimental Result:

According to the administration proposal, all the above compounds can obviously inhibit the growth of S180 sarcoma transplanted tumor in mice, and it is observable around the eighth day after drug administration that, by comparison, position 4' ethoxydiphenylethane derivatives ECB1P, ECB1GN hydrochloride and ECB1SN hydrochloride as well as position 4' ethoxydiphenylethylene positive control compounds ECA4P and ECA4GN hydrochloride both achieve the tendency of tumor shrinkage in drug administered group, reach over 60% of the tumor inhibiting rate in case of 50mg/kg dose and have fundamentally equivalent therapeutic effects, which are obviously superior to the therapeutic effects, i.e. about 40% of the tumor inhibiting rate, of methoxy positive controls CB1GN hydrochloride, CB1P and CA4P in case of 100mg/kg dose.

Tumor-inhibiting Rate (%) of Intravenous Injection Tested Drugs to 8180 Sarcoma Transplanted Tumor in Mice Embodiment 15 (Acute Toxicity Test of Single Mice Intraperitoneal Injection Tested Drugs)

1. Test Method

Kunming mice (half-and-half male and female, 17 to 22 grams heavy) are randomly grouped according to weights thereof, and during the test, the mice are divided, based on the proportion of 0.9, into 10 dose groups with each including 10 mice and having the maximal dose of 1500 mg/kg, the tested drugs having the respective doses of 1500, 1350, 1215, 1093, 984, 885, 797, 717, 645 and 581 mg/kg are administered in a manner of single intraperitoneal injection, mice observation and death rate recording are respectively performed once 0.25 h, 0.5 h, 1 h, 2 h, 4 h and 24 h after the drug administration, afterwards, everyday mice observation and death rate recording are performed for 14 days, the mice that are not dead are executed on the fifteenth day and are subjected to pathological anatomy.

2. Test Result

Single intraperitoneal injection administration at high dose causes the death of mice 40 minutes and 1 hour later, obvious residual liquid is not found after dissection, indicating the fast absorption of the drugs, and the other mice mainly die 1 to 2 days after the administration, no death of mice is observed after the fifth day, no abnormality of the heart, lung, liver, spleen, kidney and other organs in dead mice is found through dissection, and the surviving mice suffer from diarrhea not severe, which indicates that the tested drugs mainly lead to acute toxic response without obvious delayed toxicity, therefore, the result of the test shows that ethoxydiphenylethane compounds ECB1P, ECB1GN hydrochloride and ECB1SN hydrochloride have the toxicity lower than ethoxydiphenylethylene positive control compounds ECA4P and ECA4GN hydrochloride in administration group.-

| Group | ECB1P | | ECB1GN hydrochloride | | ECB1SN hydrochloride | | ECA4P | | ECA4GN hydrochloride | | CB1GN hydrochloride | | CB1P | | CA4P | |
|---|---|---|---|---|---|---|---|---|---|---|---|---|---|---|---|---|
| Dose(mg/kg) | 25 | 50 | 25 | 50 | 25 | 50 | 25 | 50 | 25 | 50 | 50 | 100 | 50 | 100 | 50 | 100 |
| Tumor-inhibiting rate (%) | 42 | 65 | 40 | 63 | 45 | 66 | 43 | 69 | 39 | 64 | 26 | 43 | 28 | 38 | 28 | 42 |

Result of Acute Toxicity Test of Single Mice Intraperitoneal Injection Tested Drugs

|  | ECB1P | ECB1GN hydrochloride | ECB1SN hydrochloride | ECA4P | ECA4GN hydrochloride | CB1P | CA4P |
|---|---|---|---|---|---|---|---|
| LD50 (mg/kg) | 1056 | 1012 | 1185 | 906 | 912 | 1228 | 1276 |
| 95% confidence limit | 815-1392 | 787-1296 | 840-1338 | 714-1186 | 654-1208 | 1050-1438 | 1047-1455 |

The invention claimed is:

1. An ethoxydiphenylethane derivative, characterized in that the structure thereof is shown as the formula (I):

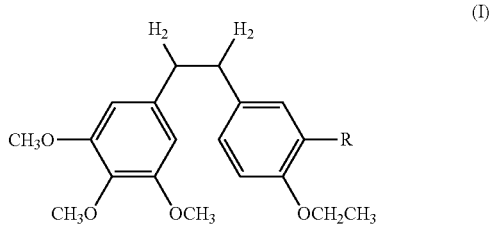

wherein R is hydroxy, amino, phosphate, sulfate, choline phosphate, or amino acid side chain and water soluble ammonium salt thereof.

2. The compound according to claim 1, characterized in that the R is hydroxy, amino, disodium phosphate salt, ammonium phosphate salt, sulfate salt, choline phosphate inner salt, natural amino acid side chain and water soluble ammonium salt thereof, or —NH(COCHR'NH)m-H (wherein R', is hydrogen, phenyl, and m represents an integer from 1 to 3) and water soluble ammonium salt thereof.

3. The compound according to claim 1, characterized in that the R is —OH, —NH$_2$, —OPO$_2$Na$_2$, —NHCOCH$_2$NH$_2$ or —NHCOCHNH$_2$CH$_2$OH.

4. A preparation method of the compound according to claim 1, characterized in that the method comprises the following steps that:
   (1) the 4-ethoxy-3-hydroxybenzaldehyde (IV) is prepared to 4-ethoxy-3-benzyloxybenzaldehyde (V) by benzyl chloride;
   (2) 3,4,5-trimethoxy triphenyl benzylidene bromide phosphonium bromide tetrahydrofuran solution and 4-ethoxy-3-benzyloxybenzaldehyde are subjected to vinylation addition under the addition of potassium tert-butoxide in order to synthesize 3,4,5-trimethoxy-3'-benzyloxy-4'-ethoxydiphenylethylene (VI);
   (3) the 3,4,5-trimethoxy-3'-henzyloxy-4'-ethoxydiphenylethylene (VI) is hydrogenated under palladium-carbon to hydrogenate olefinic bonds, and debenzylation is performed to obtain 3,4,5-trimethoxy-3'-hydroxy-4'-ethoxydiphenylethane (VII).

5. The preparation method of the compound according to claim 4, characterized in that the method comprises the following steps that:
   (1) under phase transfer catalysis, 4-hydroxy-3-methoxybenzaldehyde (II) is subjected to ethoxylation by bromethyl to form 4-ethoxy-3-methoxybenzaldehyde (III);
   (2) meta-methyl is selectively removed by lithium diphenylphosphide and converted to hydroxy in order to obtain 4-ethoxy-3-hydroxybenzaldehyde (IV);
   (3) the 4-ethoxy-3-hydroxybenzaldehyde (IV) is prepared to 4-ethoxy-3-benzyloxybenzaldehyde (V) by benzyl chloride;
   (4) 3,4,5-trimethoxy triphenyl benzylidene bromide phosphonium bromide tetrahydrofuran solution and 4-ethoxy-3-berrzyloxybenzaldehyde are subjected to vinylation addition under the addition of potassium tert-butoxide in order to synthesize 3,4,5-trimethoxy-3'-benzyloxy-4'-ethoxydiphenylethylene (VI); and
   (5) the 3,4,5-trimethoxy-3'-benzyloxy-4'-ethoxydiphenylethylene (VI) is hydrogenated under palladium-carbon to hydrogenate olefinic bonds, and debenzylation is performed to obtain 3,4,5-trimethoxy-3'-hydroxy-4'-ethoxydiphenylethane (VII).

6. The preparation method of the compound according to claim 4, characterized in that the 3,4,5-trimethoxy-3'-hydroxy-4'-ethoxydiphenylethane (VII) is subjected to phosphorylation, phosphate esterification and sulfation to form ethoxyhydroxydiphenylethane water soluble derivative: disodium phosphate salt, sulfate salt, ammonium phosphate salt or choline phosphate inner salt.

7. The preparation method of the compound according to claim 6, characterized in that the 3,4,5-trimethoxy-3'-hydroxy-4'-ethoxydiphenylethane (VII) forms 3,4,5-trimethoxy-4'-ethoxydiphenylethane-3'-o-disodium phosphate salt (VII) under the action of phosphorylation agent phosphorus oxychloride and 2 mol/L, of NaOH.

8. The preparation method of the compound according to claim 6, characterized in that the 3,4,5-trimethoxy-3'-hydroxy-4'-ethoxydiphenylethane (VII) is reacted with dibenzyl phosphate to form benzyl phosphate, and sodium methoxide/absolute methanol is added under trimethyibromosilane (TMBS) to obtain 3,4,5-trimethoxy-4'-ethoxydiphertylethane-3'-o-disodium phosphate salt.

9. The preparation method of the compound according to claim 1, characterized in that the method further comprises the following steps that:
   (1) trimethoxyphenyl bromide triplienylphosphonium methylide and the 4-ethoxy-3-nitrobenzaldehyde (X) are subjected to Wittig reaction to generate 3,4,5-trimethoxy-3'-nitryl-4'-ethoxydiphenylethylene (XI);
   (2) the 3,4,5-trimethoxy-3'-nitryl-4'-ethoxydiphenylethylene (XI) is subjected to hydrogenation reduction under palladium-carbon catalyst/sodium borohydride to reduce nitryl to amino and reduce olefinic bonds to ethane single bonds, so as to obtain 3,4,5-trimethoxy-3'-amino-4'-ethoxydiphenylethane (XII).

10. The preparation method of the compound according to claim 9, characterized in that the method further comprises the following steps that:
    (1) under phase transfer catalysis, 4-hydroxy-3-nitrobenzaldehyde (IX) is subjected to ethoxylation by bromethyl to form 4-ethoxy-3-nitrobenzaldehyde (X);
    (2) trimethoxyphenyl bromide triphenylphosphonium methylide and the 4-ethoxy-3-nitrobenzaldehyde (X) are subjected to Wittig reaction to generate 3,4,5-trimethoxy-3'-nitryl-4'-ethoxydiphenylethylene (XI); and
    (3) the 3,4,5-trimethoxy-3'-nitryl-4'-ethoxydiphenylethylene (XI) is subjected to hydrogenation reduction under palladium-carbon catalyst/sodium borohydride to reduce nitryl to amino and reduce oletinic bonds to ethane single bonds, so as to obtain 3,4,5-trimethoxy-3'-amino-4'-ethoxydiphenylethane (XII).

11. The preparation method of the compound according to claim 9, characterized in that the 3,4,5-trimethoxy-3'-amino-4'-ethoxydiphenylethane (XII) and amino acid derivatives are subjected to reaction to form ethoxyaminodiphenylethane amino acid amide derivative having the amino acid amide side chain selected from the group consisting of natural amino acid side chain, and —NH(COCHR'NH)m-H (wherein R' is hydrogen, phenyl, and m represents an integer from 1 to 3).

12. The preparation method of the compound according to claim 11, characterized in that under the catalysis of dicyclohexylcarbo-diimide (DCC) and 1-hydroxybenzotrizole (HOBt) or hexafluorophosphatebenzotrizole-1-yl-oxo-tri(dimethylamino)phosphor(BOP agent), the 3,4,5-trimethoxy-3'-amino-4'-ethoxydiphenylethane (XII) is reacted with N-a-9-fluorenylinethoxycarbonyl amino acid derivative (Fmoc AA), amino at position 3' is converted into Fmoc-amino acid amide, Fmoc is removed to generate ethoxydiphenylethane amino acid amide derivatives, which respectively are 3,4,5-trimethoxy-3'-glycylamino-4'-ethoxydiphenylethane (XIII) and 3,4,5-trimethoxy-3'-serylamino-4'-ethoxydiphenylethane (XIV), 13. The preparation method of the compound according to claim 11, characterized in that the amino acid amide derivatives are dissolved in methanol, ethanol or isopropanol, and the equivalent amount of hydrochloric acid, sulfuric acid or phosphoric acid as well as petroleum ether or n-hexane are added to dilute the derivatives to form water soluble ammonium salt.

14. The preparation method of the compound according to claim 12, characterized in that the amino acid amide derivatives are dissolved in methanol, ethanol or isopropanol, and the equivalent amount of hydrochloric acid, sulfuric acid or phosphoric acid as well as petroleum ether or n-hexane are added to dilute the derivatives to form water soluble ammonium salt.

15. The compound according to claim 1, characterized in that the pharmaceutical preparation thereof is selected from the group consisting of lyophiled powder, powder, injection, liposome, emulsion, micro-capsule, suspension or solution, administered in the form of intravenous injection, granule, tablet, capsule, syrup, administered orally, and a suppository.

16. The compound according to claim 1, characterized by the use of the compound of the formula (I) in preparing a tubulin aggregation inhibitor.

17. The compound according to claim 16, characterized by the use of the compound of the formula (I) in preparing medicines having, as anti-tumor angiolysis agent, vascular target effect for various tumors.

18. The compound according to claim 16, characterized by the use of the compound of the formula (I) in preparing medicines for the treatment of diseases caused by abnormal angiogenesis.

* * * * *

UNITED STATES PATENT AND TRADEMARK OFFICE
CERTIFICATE OF CORRECTION

PATENT NO. : 8,686,187 B2  
APPLICATION NO. : 13/124504  
DATED : April 1, 2014  
INVENTOR(S) : Wu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 411 days.

Signed and Sealed this

Twenty-ninth Day of September, 2015

Michelle K. Lee  
*Director of the United States Patent and Trademark Office*